United States Patent [19]

Sandermann et al.

[11] 4,122,185
[45] Oct. 24, 1978

[54] 2-PHENYL- AND 2-BENZYL-N-[(TRICHLOROMETHYL)THIO]SUCCINIMIDES, AND FUNGICIDAL COMPOSITIONS THEREOF

[75] Inventors: Wilhelm Sandermann, Donaustauf; Heinz Eggensperger, Hamburg; Karl-Heinz Diehl, Norderstedt, all of Germany

[73] Assignee: Sterling Drug Inc., New York, N.Y.

[21] Appl. No.: 820,635

[22] Filed: Aug. 1, 1977

[30] Foreign Application Priority Data

Aug. 11, 1976 [DE] Fed. Rep. of Germany ....... 2636076

[51] Int. Cl.$^2$ ..................... A01N 9/12; C07D 207/40
[52] U.S. Cl. ............................ 424/274; 260/326.5 S; 260/326 H
[58] Field of Search ..................... 260/326.5 S, 326 H; 424/274

[56] References Cited

U.S. PATENT DOCUMENTS 2,553,770  5/1951  Killleson .................. 260/326.5 S

FOREIGN PATENT DOCUMENTS 1,099,299  1/1968  United Kingdom.

OTHER PUBLICATIONS

Owens et al., Contribs Boyce Thompson 20, 171–190, (1959).
Fischer et al., Chem. Abs. 55, 27196d, (1961).
B.A.S.F, Chem. Abs. 59, 9836E, (1963).

*Primary Examiner*—Donald G. Daus
*Assistant Examiner*—Mark L. Berch
*Attorney, Agent, or Firm*—Frederik W. Stonner; B. Woodrow Wyatt

[57] ABSTRACT

N-[(Trichloromethyl)thio]succinimides of the formula

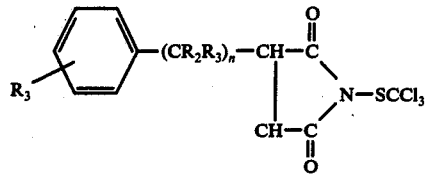

where $R_1$, $R_2$ and $R_3$ independently are hydrogen or alkyl having from 1 to 6 carbon atoms, and n is zero or the integer 1, having antifungal activity, a method of use thereof as antifungal agents, and antifungal compositions comprising them are disclosed.

21 Claims, No Drawings

2-PHENYL- AND 2-BENZYL-N-[(TRICHLOROMETHYL)THIO]SUCCINIMIDES, AND FUNGICIDAL COMPOSITIONS THEREOF

BACKGROUND OF THE INVENTION

1. Field of the Invention

The invention relates to novel 2-phenyl- and 2-benzyl-N-[(trichloromethyl)thio]succinimides having antifungal activity, to a method for their use as antifungal agents, and to antifungal compositions comprising them as active ingredients.

2. Description of the Prior Art

Fungicides find application as plant protectants, for the preservation of wood, leather, lacquer, textiles, paper and other organic materials, and in combating fungus infections in animals and man. Many of these fungicides, however, have certain disadvantages. Thus, organic mercury compounds are toxic, organic tin compounds are light sensitive, chlorophenols such as pentachlorophenol are volatile and toxic to man, and derivatives of dithiocarbamic acids react with metal siccatives in lacquers thus causing discoloration.

U.S. Pat. No. 2,553,770 discloses, as fungicides, germicides and insecticides, a class of N-[(trichloromethyl)thio] compounds represented by the general structural formula:

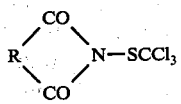

where R is defined as an organic residue which may be aliphatic, aromatic, alicyclic, heterocyclic and substituted derivatives of such organic residues. Exemplary of compounds disclosed are N-[(trichloromethyl)thio]imides of the following structures:

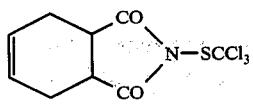
I

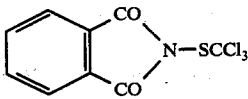
II

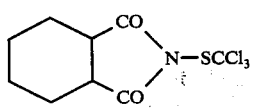
III

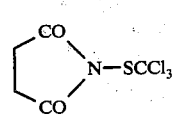

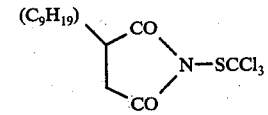

Compounds I (captan), II (phaltan; folpet) and III are presently items of commerce. The mechanism of action of captan is apparently due to the blocking of the SH groups of phosphorylating enzymes, cf. R. G. Owens and H. M. Novotny, Contribs. Boyce Thompson Inst. 20, 171-90 (1959).

In addition to the (trichloromethyl)thio compounds, fluoro-dichlorothio compounds have also been developed as follows:

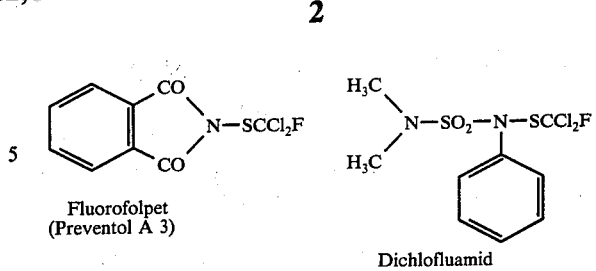

Fluorofolpet
(Preventol A 3)

Dichlofluamid

CA 55, 27196d (1961) [J. prakt. Chem. 12, 172-6 (1961)] describes the preparation of 2-anilino- and 2-(4-methylanilino)-N-[(trichloromethyl)thio]succinimide. There is no disclosure in this reference of antimicrobial activity.

CA 59, 9836e (1963) (German Pat. No. 1,145,420) describes the preparation of N[(trichloromethyl)thio]-α,α-pentamethylene-succinimide and its utility as a broad spectrum fungicide.

CA 69, P35497U (1968) (British Pat. No. 1,099,299) describes N-[(polyhaloalkyl)thio]alkenylsuccinimides, e.g., N-[(trichloromethyl)thio]-2-allylsuccinimide, having utility as fungicides.

None of the foregoing disclosed references describe or suggest N-[(trichloromethyl)thio]succinimides mono-substituted at the 2-position by phenyl or benzyl.

In the development of new fungicides, certain properties are desirable. Thus a fungicide should desirably meet all of the following criteria: (1) be innocuous to man, (2) have high activity of long duration, and (3) possess a broad spectrum of activity.

Since fungicides of the class of N-[(trichloromethyl)thio]dicarboximides fulfill the requirement of long duration of activity, extensive investigations have been carried out with the purpose of finding new compounds of that class which possess a broad spectrum of activity and which are innocuous to man. With respect to the latter, in recent years certain N-[(trichloromethyl)thio] compounds such as captan (I) and folpet (II) have become suspect as producing malformation-causing mutations, cf. "Umschau", 1970, p. 652 and P. Schulster, "Die Zeit", Jan. 4, 1974. Apparently the phthalimide structure of these fungicides is responsible for the detrimental effects. Thus the discovery of new compounds of this class which do not possess the phthalimide structure but which possess high fungicidal activity is of paramount importance.

It was found that of a large number of synthetically prepared compounds, by no means all compounds of the general structural formula

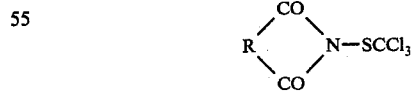

as defined in U.S. Pat. No. 2,553,770 noted hereinabove display fungicidal activity. Rather, activity is associated with strictly defined structural features. Thus, the trichloromethylthio compounds obtained from anthracene-maleic anhydride adduct, caryophyllen-maleic anhydride adduct, isoeugenol-maleic anhydride adduct, homophthalic anhydride, camphoric anhydride, hexadecyl succinic anhydride and many other anhydrides are inactive.

SUMMARY OF THE INVENTION

After considerable experimentation resulting in compounds having poor or no fungicidal activity and in physiologically hazardous compounds, a class of compounds was discovered which unexpectedly possesses favorable properties.

Thus in the compound aspect of the invention there is provided an N-[(trichloromethyl)thio]succinimide having the structural formula

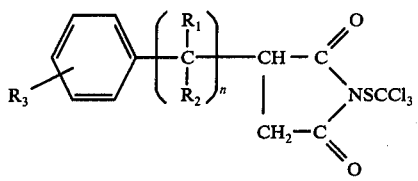

where $R_1$, $R_2$ and $R_3$ independently are hydrogen or alkyl having from 1 to 6 carbon atoms, and $n$ is zero or the integer 1.

The compounds of the invention are excellent fungicides possessing a broad spectrum of fungicidal activity.

In a composition aspect of the invention there is provided a fungicidal composition comprising as fungicidal ingredient at least one N-[(trichloromethyl)thio]succinimide having the structural formula

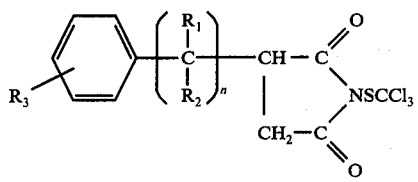

where $R_1$, $R_2$ and $R_3$ independently are hydrogen or alkyl having from 1 to 6 carbon atoms, and $n$ is zero or the integer 1, and a carrier therefor.

In a method aspect of the invention there is provided a method for preventing or retarding the deleterious effects associated with fungal contamination of a material susceptible to fungal contamination which comprises treating the material with a fungicidally effective amount of at least one N-[(trichloromethyl)thio]succinimide having the structural formula

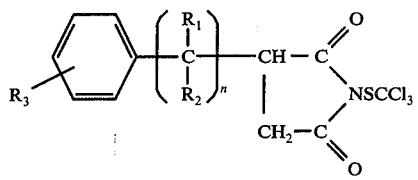

where $R_1$, $R_2$ and $R_3$ independently are hydrogen or alkyl having from 1 to 6 carbon atoms, and $n$ is zero or the integer 1.

Throughout the specification it will be understood that alkyl, as represented by $R_1$, $R_2$ and $R_3$ in the structural formula of the compounds of the invention, can be straight or branched.

DETAILED DESCRIPTION INCLUSIVE OF THE PREFERRED EMBODIMENTS

The compounds of the invention are prepared using generally known procedures. Thus a succinic anhydride represented by the general structural formula

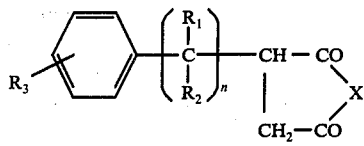

where $X=O$ and $R_1$, $R_2$, $R_3$ and $n$ have the meanings defined hereinbefore, is converted to the corresponding imide ($X=NH$) which then is reacted with trichloromethanesulfenyl chloride to give the compound of the invention.

GENERAL PROCEDURE USED FOR PREPARING THE COMPOUNDS OF THE INVENTION

The appropriate 2-benzyl- or 2-phenyl succinic anhydride (1 mole) was slowly heated with 200 ml. of ammonium hydroxide (s.g. 0.91) to 250° C. until ammonia was no longer liberated, using a condenser of a length which allowed ready evaporation of water. The resulting corresponding succinimide was dissolved in 500 ml. of 2N ethanolic sodium hydroxide, the ethanol was distilled off in vacuo, and the resulting sodium salt of the imide was suspended in 500 ml of dioxane. To this suspension was added slowly, with gentle stirring, trichloromethanesulfenyl chloride (1.1 moles) in 200 ml. of dioxane and the reaction mixture was heated for thirty minutes at 80° C. The mixture was allowed to stand overnight, filtered from sodium chloride, and concentrated in vacuo to give the corresponding N-[(trichloromethyl)-thio]succinimide which, if necessary, was recrystallized from ethanol or benzene.

Following the above-described procedure and reacting with ammonia hydroxide the following 2-benzyl- and 2-phenylsuccinic anhydrides:

2-phenylsuccinic anhydride,
2-benzylsuccinic anhydride,
2-(4-methylbenzyl)succinic anhydride,
2-(4-tert-butylbenzyl)succinic anhydride,
2-(α-methylbenzyl)succinic anhydride,
2-(α,α-dimethylbenzyl)succinic anhydride and
2-(4-isopropyl-α,α-dimethylbenzyl)succinic anhydride
there was obtained respectively:
2-phenylsuccinimide,
2-benzylsuccinimide,
2-(4-methylbenzyl)succinimide,
2-(4-tert-butylbenzyl)succinimide,
2-(α-methylbenzyl)succinimide,
2-(α,α-dimethylbenzyl)succinimide and
2-(4-isopropyl-α,α-dimethylbenzyl)succinimide
which, on reaction with trichloromethanesulfenyl chloride yielded respectively the final products of Examples 1 to 7

EXAMPLE 1

N-[(Trichloromethyl)thio]-2-phenylsuccinimide

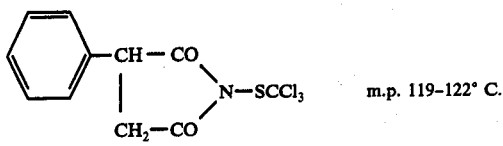 m.p. 119–122° C.

EXAMPLE 2

N-[(Trichloromethyl)thio]-2-benzylsuccinimide

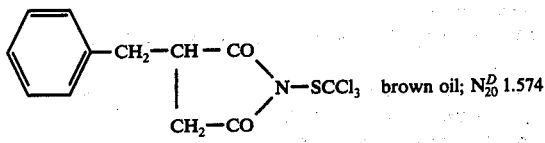 brown oil; $n_{20}^D$ 1.574

EXAMPLE 3

N-[(Trichloromethyl)thio]-2-(4-methylbenzyl)succinimide

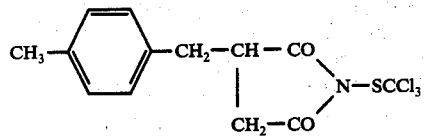

EXAMPLE 4

N-[(Trichloromethyl)thio]-2-(4-tert-butylbenzyl)-succinimide

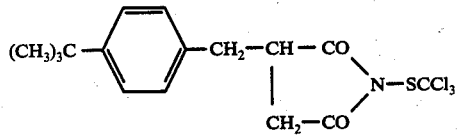

EXAMPLE 5

N-[(Trichloromethyl)thio]-2-(α-methylbenzyl)-succinimide

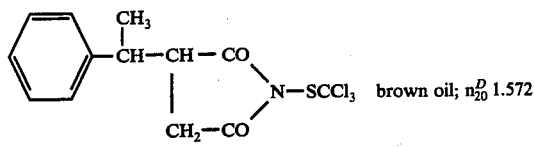 brown oil; $n_{20}^D$ 1.572

EXAMPLE 6

N-[(Trichloromethyl)thio]-2-(α,α-dimethylbenzyl)-succinimide

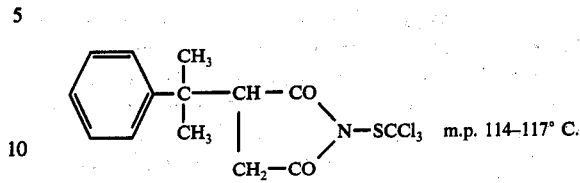 m.p. 114–117° C.

EXAMPLE 7

N-[(Trichloromethyl)thio]-2-(4-isopropyl-α,α-dimethylbenzyl)succinimide

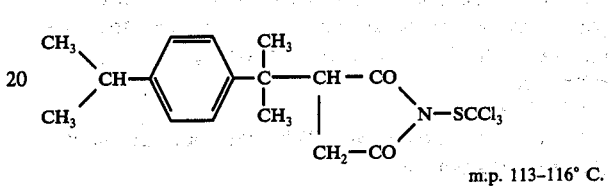

m.p. 113–116° C.

The 2-phenylsuccinic anhydrides used as starting materials are known compounds or can be prepared by known procedures. Thus they can be prepared from the corresponding 2-phenylsuccinic acids by standard dehydration procedures. The 2-phenylsuccinic acids can be prepared from the corresponding 2-cyano-3-phenylacrylic acids according to the procedure described in Organic Syntheses 8, 88–90 (1928). The 2-cyano-3-phenylacrylic acids can be prepared by reaction of an appropriate benzaldehyde with cyanoacetic acid according to the procedure described in Organic Syntheses 7, 20–22 (1927).

The 2-benzylsuccinic anhydride starting materials are known compounds or can be prepared by known procedures, e.g., by reaction of maleic anhydride and appropriate alkyl substituted benzenes according to the procedure described in J. Org. Chem. 21, 1473–7 (1956).

The compounds of Examples 1 to 7, and for comparison also the known fungicide captan (I), were tested to determine their minimum inhibitory concentration (MIC) with respect to several microorganisms. The results are tabulated below.

| Compound | Minimum Inhibitory Concentration (%) Microorganism | | | | | |
|---|---|---|---|---|---|---|
| | 1 | 2 | 3 | 4 | 5 | 6 |
| Example 1 | 0.05 | 0.005 | 0.05 | 0.0001 | 0.0001 | 0.0001 |
| Example 2 | 0.1 | 0.05 | 0.05 | 0.05 | 0.01 | 0.05 |
| Example 3 | 0.05 | 0.005 | 0.005 | 0.005 | 0.005 | 0.005 |
| Example 4 | 0.1 | 0.005 | 0.05 | 0.05 | 0.01 | 0.005 |
| Example 5 | 0.1 | 0.1 | 0.01 | 0.005 | 0.01 | 0.005 |
| Example 6 | 1 | 0.005 | 1 | 0.01 | 0.01 | 0.001 |
| Example 7 | 1 | 0.01 | 0.01 | 0.01 | 0.05 | 0.005 |
| captan (II) | 0.05 | 0.01 | 0.05 | — | 0.005 | — |

1 *Staphylococcus aureus*
2 *Penicillium glaucum*
3 *Aspergillus niger*
4 *Sclerophoma pityophila*
5 *Pullularia pullulans*
6 *Saccharomyces cerevisiae*

The compounds of the invention are active fungicides which can be incorporated in materials susceptible to fungal contamination to retard or prevent fungal growth. For example they can be employed as active fungicidal ingredients in oil-based paints, wood, leather, textiles, tent canvas, cardboard and paper against the deleterious effects of fungus. For such purpose, solutions in organic solvents as well as combinations with waxes, such as paraffin, are employed.

The compounds of the invention can be prepared for use using conventional techniques. Thus they may be mixed with a suitable carrier, e.g., a solid carrier such as but not limited to clay, talc and bentonite; or with a suitable liquid carrier, e.g., as a solution in a solvent such as but not limited to petroleum hydrocarbons and alcohol, and as suspensions in a non-solvent.

The amounts of the compounds or mixtures thereof to be applied in order to be fungicidally effective will range from about 0.0001 to about 1 percent by weight of the material to be protected. The specific concentration will vary depending on a number of factors, for example, on the nature of the material to be protected, and can readily be determined by one having ordinary skill in the art.

We claim:

1. An N-[(trichloromethyl)thio]succinimide having the structural formula

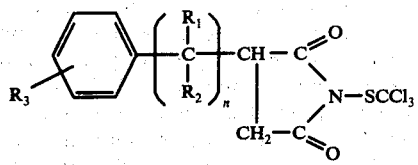

where $R_1$, $R_2$ and $R_3$ independently are hydrogen or alkyl having from 1 to 6 carbon atoms, and $n$ is zero or the integer 1.

2. An N-[(trichloromethyl)thio]succinimide according to claim 1 where $R_1$, $R_2$ and $R_3$ independently are hydrogen or alkyl having from 1 to 4 carbon atoms.

3. An N-[(trichloromethyl)thio]succinimide according to claim 2 where $n$ is zero.

4. N-[(Trichloromethyl)thio]-2-phenylsuccinimide according to claim 3.

5. An N-[(trichloromethyl)thio]succinimide according to claim 2 where $n$ is the integer 1.

6. An N-[(trichloromethyl)thio]succinimide according to claim 5 where $R_1$ and $R_2$ independently are hydrogen or methyl.

7. A compound according to claim 6 selected from the group consisting of N-[(trichloromethyl)thio]-2-benzylsuccinimide, N-[(trichloromethyl)thio]-2-(4-methylbenzyl)succinimide, N-[(trichloromethyl)thio]-2-(4-tert-butylbenzyl)succinimide, N-[(trichloromethyl)thio]-2-(α-methylbenzyl)succinimide, N-[(trichloromethyl)thio]-2-(α,α-dimethylbenzyl)succinimide and N-[(trichloromethyl)thio]-2(-isopropyl-α,α-dimethylbenzyl)succinimide.

8. A fungicidal composition consisting of a fungicidally effective amount of at least one N-[(trichloromethyl)thio]succinimide having the structural formula

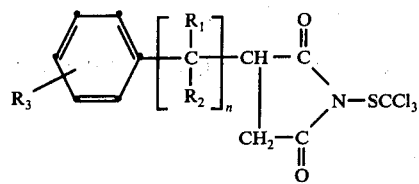

where $R_1$, $R_2$ and $R_3$ independently are hydrogen or alkyl having from 1 to 6 carbon atoms, and $n$ is zero or the integer 1, and a carrier therefor.

9. A composition according to claim 8 where $R_1$, $R_2$ and $R_3$ independently are hydrogen or alkyl having from 1 to 4 carbon atoms.

10. A composition according to claim 9 where $n$ is zero.

11. A composition according to claim 10 comprising N-[(trichloromethyl)thio]-2-phenylsuccinimide as fungicidal ingredient.

12. A composition according to claim 9 where $n$ is the integer 1.

13. A composition according to claim 12 where $R_1$ and $R_2$ independently are hydrogen or methyl.

14. A composition according to claim 13 comprising as fungicidal ingredient at least one N-[(trichloromethyl)thio]-succinimide selected from the group consisting of N-[(trichloromethyl)thio]-2-benzylsuccinimide, N-[(trichloromethyl)thio]-2-(4-methylbenzyl)succinimide, N-[(trichloromethyl)thio]-2-(4-tert-butylbenzyl)succinimide, N-[(trichloromethyl)thio]-2-(α-methylbenzyl)succinimide, N-[(trichloromethyl)thio]-2-(α,α-dimethylbenzyl)succinimide and N-[(trichloromethyl)thio]-2-(4-isopropyl-α,α-dimethylbenzyl)succinimide.

15. A method for preventing or retarding the deleterious effects associated with fungal contamination of a material susceptible to fungal contamination which comprises treating the material with a composition according to claim 8.

16. A method according to claim 15 where $R_1$, $R_2$ and $R_3$ independently are hydrogen or alkyl having from 1 to 4 carbon atoms.

17. A method according to claim 16 where $n$ is zero.

18. A method according to claim 17 where the material is treated with N-[(trichloromethyl)thio]-2-phenylsuccinimide.

19. A method according to claim 16 where $n$ is the integer 1.

20. A method according to claim 19 where $R_1$ and $R_2$ independently are hydrogen or methyl.

21. A method according to claim 20 wherein the material is treated with at least one N-[(trichloromethyl)thio]succinimide selected from the group consisting of N-[(trichloromethyl)thio]-2-benzylsuccinimide, N-[(trichloromethyl)thio]-2-(4-methylbenzyl)-succinimide, N-[(trichloromethyl)thio]-2-(4-tert-butylbenzyl)-succinimide, N-[(trichloromethyl)thio]-2-(α-methylbenzyl)-succinimide, N-[(trichloromethyl)thio]-2-(α,α-dimethylbenzyl)succinimide and N-[(trichloromethyl)thio]-2-(4-isopropyl-α,α-dimethylbenzyl)succinimide.

* * * * *